United States Patent [19]

Hüschelrath et al.

[11] Patent Number: 4,628,261
[45] Date of Patent: Dec. 9, 1986

[54] METHOD AND APPARATUS FOR SEPARATING MAGNETIC FIELD ATTRIBUTABLE TO FLAWS IN A MATERIAL FROM MAGNETIC FIELDS ATTRIBUTABLE TO OTHER PHENOMENA

[75] Inventors: Gerhard Hüschelrath, Laufach-Frohnhofen; Ursula Ruth, Ronneburg, both of Fed. Rep. of Germany

[73] Assignee: Nukem GmbH, Hanau, Fed. Rep. of Germany

[21] Appl. No.: 482,284

[22] Filed: Apr. 5, 1983

[30] Foreign Application Priority Data

Apr. 8, 1982 [DE] Fed. Rep. of Germany ....... 3213267

[51] Int. Cl.⁴ .................. G01N 27/90; G01R 33/12
[52] U.S. Cl. .................................. 324/240; 324/227; 324/262; 364/507
[58] Field of Search ............... 324/202, 225, 226, 227, 324/228–234, 239, 240–243, 260–262, 235–238; 364/551, 552, 481, 571, 507

[56] References Cited

U.S. PATENT DOCUMENTS

| | | | |
|---|---|---|---|
| 3,302,105 | 1/1967 | Libby et al. | 324/233 |
| 3,895,290 | 7/1975 | Audenard et al. | 324/233 |
| 3,904,957 | 9/1975 | Griese | 324/233 |
| 4,059,795 | 11/1977 | Mordwinkin | 324/233 |
| 4,061,968 | 12/1977 | Pigeon | 324/234 |
| 4,121,289 | 10/1978 | Stiel | 364/552 |
| 4,207,520 | 6/1980 | Flora et al. | 324/233 X |
| 4,210,904 | 7/1980 | Renzel et al. | 364/507 X |
| 4,230,987 | 10/1980 | Mordwinkin | 324/233 X |
| 4,322,683 | 3/1982 | Vieira et al. | 324/233 X |
| 4,349,880 | 9/1982 | Southgate et al. | 364/507 |
| 4,403,294 | 9/1983 | Hamada et al. | 364/507 |
| 4,437,164 | 3/1984 | Branch, III | 364/571 |
| 4,450,405 | 5/1984 | Howard | 324/228 X |
| 4,455,529 | 6/1984 | Sinclair | 324/339 |
| 4,462,083 | 7/1984 | Schwefel | 364/571 X |
| 4,485,451 | 11/1984 | Dyakov et al. | 364/551 |

FOREIGN PATENT DOCUMENTS

| | | |
|---|---|---|
| 2913877 | 10/1979 | Fed. Rep. of Germany . |
| 2937865 | 4/1981 | Fed. Rep. of Germany . |
| 3029936 | 3/1982 | Fed. Rep. of Germany . |
| 0068503 | 6/1982 | Fed. Rep. of Germany . |
| 2010492 | 6/1979 | United Kingdom . |

OTHER PUBLICATIONS

"Eddy Current In-Situ Inspection of Ferromagnetic Monel Tubes", by V. S. Cecco and C. R. Bax, Sept. 1973, pp.1–4, Chalk River Laboratories, Chalk River, Ontario, Canada.

*Primary Examiner*—Reinhard J. Eisenzopf
*Assistant Examiner*—Warren S. Edmonds
*Attorney, Agent, or Firm*—Cushman, Darby & Cushman

[57] ABSTRACT

A method and an apparatus for testing materials using the eddy current principle enables a better exploitation of the sensitivity of measurement. Initially, the complex values appearing during a test cycle are examined as to whether only disturbance signals, disturbance signals in connection with flaw signals, or only flaw signals are present. The complex values are selectively further processed directly if there are flaw signals only, or are further processed for disturbance signal elimination. The direct further processing as well as the further processing made after elimination of the disturbance signal comprises the determination of the type of flaw and the depth of the flaw.

14 Claims, 3 Drawing Figures

METHOD AND APPARATUS FOR SEPARATING MAGNETIC FIELD ATTRIBUTABLE TO FLAWS IN A MATERIAL FROM MAGNETIC FIELDS ATTRIBUTABLE TO OTHER PHENOMENA

FIELD OF THE INVENTION

The invention relates to a method and an apparatus for testing materials for flaws with the eddy current principle.

BACKGROUND OF THE INVENTION

To test a material with the eddy current method, a coil is moved into proximity with a test piece, the coil inducing eddy currents in the test piece by producing magnetic alternating fields. Such induced eddy currents produce a secondary field in the coil or in a respective sensor coil. The signals appearing during a scanning cycle at the output of the coil or sensor coil are converted into a sequence of digital values corresponding to complex numbers.

During the testing of materials with the eddy current method, very often disturbing effects will appear, generating higher and/or different signal levels than those generated by the defects present in the material being tested. Such disturbance effects are caused, e.g., by the lifting of the coil from the test piece, by ferritic influx in the material, etc. In order to detect the flaws, these interfering signals must be separated from those signals caused by the defects in the material For this separation one can use the amplitudes and the phase positions of the complex values. Many times, however, it is not possible to definitely assign the flaw signals and disturbance signals to certain amplitude and phase ranges.

In a multifrequency testing apparatus, one uses linear algorithms to distinguish the flaw signals from the disturbance signals (i.e., these signals attributable to field variations produced by phenomena other than flaws in the material). Thereby stationary independent data measured at different measuring frequencies are combined by matrix operations in order to generate zero points in the directions of the disturbance producing the disturbance field to be suppressed. Flaw signals are indicated only when the phase of the disturbance signals falls within a predetermined range. As the amplitude of the disturbance signal increases, so do the phase angles relative to the direction of the disturbance. If the size of the defect influences not only the amplitude but also the phase position, this will result in losses unfavorably affecting the determination of the defect size. These losses will appear independent therefrom whether or not a disturbance signal is coinciding with a flaw signal.

SUMMARY OF THE INVENTION

It is the object of the invention to provide a method for testing materials with the eddy current principle in such a manner that signals produced by a disturbance are acquired in a separate step by storing complex values generated during a respective test cycle, which values, in dependence on the detection of disturbance signals, subsequently are further processed selectively compensating for the influence of disturbance signals. According to the invention, this object is realized by successively storing complex values produced by a plurality of test cycles of a sequence of such cycles. The respective measured values, dependent upon their order in the sequence, are tested as to whether they are, within limits determined by the properties of the test object, included in one of several predetermined ranges. Signals included in one of the ranges are attributable only to disturbance signals, signals included in another range are attributable to a combination of disturbance signals and signals attributable to a flaw in the material, and signals within a third range are attributable to signals produced by a flaw alone. The measured values are selectively evaluated for flaw signals in connection with disturbance signals after suppression of disturbance signals, or selectively for flaw signals without connection with disturbance signals, for determining the type of flaw and thereafter the size of flaw.

If no disturbance signals occur, by this method one can fully exploit the measuring sensitivity provided by a known eddy current measuring apparatus for detecting the type and size of flaws in a material. Upon detecting disturbance signals together with flaw signals, the influence of the disturbing phenomena can be suppressed. After the suppression of the disturbance signal, the type and size of flaws in a material can be obtained with less measuring sensitivity. The testing of the complex values as to their position in the predetermined ranges and as to the order of sequence of the transition to other ranges can be utilized for evaluating whether there is only a disturbance signal or only a flaw signal, or a disturbance signal together with a flaw signal.

In the preferred embodiment, a flaw signal is generated at the transition of the complex data of the sequence from one range corresponding to flaw signals only to another range corresponding to disturbance signals as well as flaw signals, and at the transition of the complex data from the range corresponding to disturbance signals as well as flaw signals to that range corresponding to flaw signals only.

The position of successive complex data in the different ranges is utilized as a criterion in order to detect in a simple manner the presence of defects or flaws in the material being tested.

Preferably the position and sequence of values with respect to the ranges are tested with approximately ten to fifteen complex values, where these values are simultaneously stored for subsequent evaluation. This number of values suffices for distinguishing between disturbance signals and flaw signals and for the later processing regarding the type and size of the defect.

In an exemplary embodiment, a range central point is given, being surrounded at equal distance by a base threshold, which excludes from evaluation those complex values existing within its limits. The dimension of the base threshold depends on the measuring sensitivity and on the quantity of the processed signals.

An apparatus in accordance with the present invention includes an eddy current testing apparatus connected, via a data channel, to a FIFO-storage device and to a further memory storing data correlating respective measured values to predetermined ranges, the stored data being indexed via addresses corresponding to the complex data. Registers are connected for storing the output signals produced by this further memory occurring in each case of adjacent measured values. The output signals are tested by a comparator for range transitions. A further register and interconnecting members for determinating the ranges traversed by the measured values are connected to the memories in a given order of sequence. The output signals of the comparator and the interconnecting members are applied to a microcomputer, by which one can control the selection of memories for determining the kinds of flaws. A respective memory determines the depths of flaws. An output channel generates an output for marking and sorting devices.

By means of the present invention, one can detect within a short time whether there is a flaw and what kind of flaw it is. Consequently, arrangements can be made during testing for the shifting of a sorting switch, or other control functions can be implemented.

BRIEF DESCRIPTION OF THE DRAWINGS

Further details, advantages and characteristics of the invention are explained more specifically in the following detailed description of an exemplary embodiment which is also shown in the accompanying drawings wherein.

DETAILED DESCRIPTION OF THE PREFERRED EMBODIMENT

Figure 1:
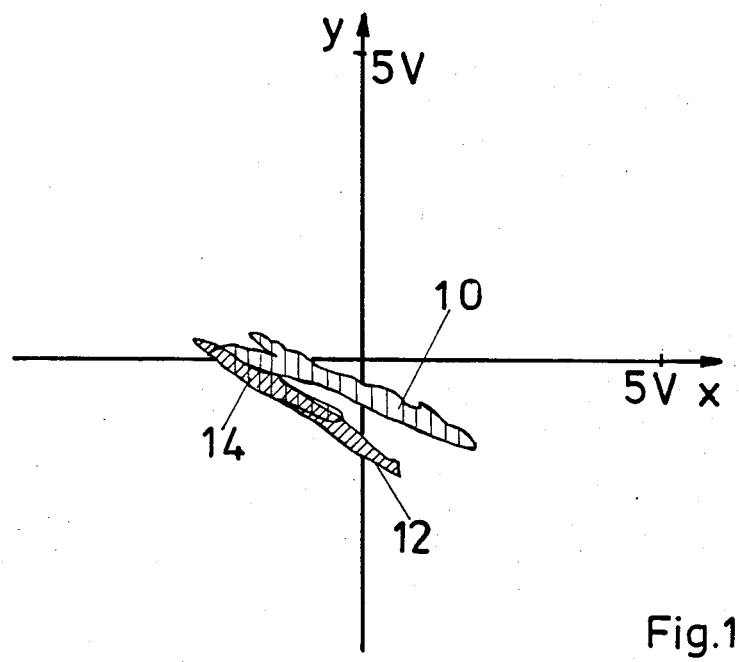
FIG. 1 is a graphical illustration of a Cartesian coordinate system showing typical areas for the position of the complex data of disturbance and flaw signals.

To test a material using the eddy current principle, an excitation coil moved in proximity to a test piece generates magnetic alternating fields, e.g. with different frequencies, in the test piece. The alternating fields induce eddy currents in the material under test, a secondary field in a respective sensor coil or in the excitation coil (which can be switched for alternate transmission and reception of magnetic flux). The output signals of the coil (or respective sensor coil) can be divided into their real and imaginary components, which are subsequently converted to digital values in a conventional fashion. A series of measured values are obtained from each measuring cycle. These values can be represented in a Cartesian coordinates system, wherein the abscissa direction indicates e.g., the real components of the value while the ordinate direction is assigned to the imaginary components. In the Cartesian coordinate system as shown in FIG. 1, the above described meanings are assigned to the abscissa and the ordinate coordinates.

For a specified test object of a given material, several test runs are initially made to obtain the flaw signals and disturbance signals typical for the object.

The obtained complex values of the flaw and disturbance signals are generally located in different ranges of the abscissa and ordinate coordinates. In FIG. 1, the range of the disturbance signals are indicated by 10 and the range of the flaw signals by 12. Ranges 10 and 12 demonstrate that the range of values of the complex disturbance and measuring signals intersect, but that they are not coextensive. Especially in case of small defects, the corresponding complex values attributable to the defects can completely fall within the intersection range of the disturbance and flaw signals. This intersection range is indicated by 14 in FIG. 1. The ranges 10, 12 and 14, in the following are also specified as features 10, 12 and 14.

The complex values obtained during a test cycle are dependent upon the frequency used for the scanning and on the testing speed. A disturbance signal attributable to a given disturbing effect will take on plural fixed values within the range 10 as the scanning frequency is changed. Only if the respective signal with a given number of complex values has taken on values within specified ranges 10, 12 and 14 can a definite assignment to a specified type of feature be made.

The chronological order of the transition between the ranges 10, 12 and 14 is of importance for characterizing the defect as being of a specified feature type. If the order of sequence changes, then no specific signal type is indicated, although the criterion for the type of a flaw in the material can be ascertained. The determination of the different signal types takes place by means of numerous complex values. Approximately ten to fifteen complex measured values are sufficient to determine whether a disturbance signal is present. These measured values, in dependence on their order of sequence, are examined as to whether they are within the limits (established for the respective test object) of those ranges corresponding only to disturbance signals, by disturbance signals and flaw signals, or only by flaw signals. At the same time, the complex values of the respective cycle are stored.

Figure 2:
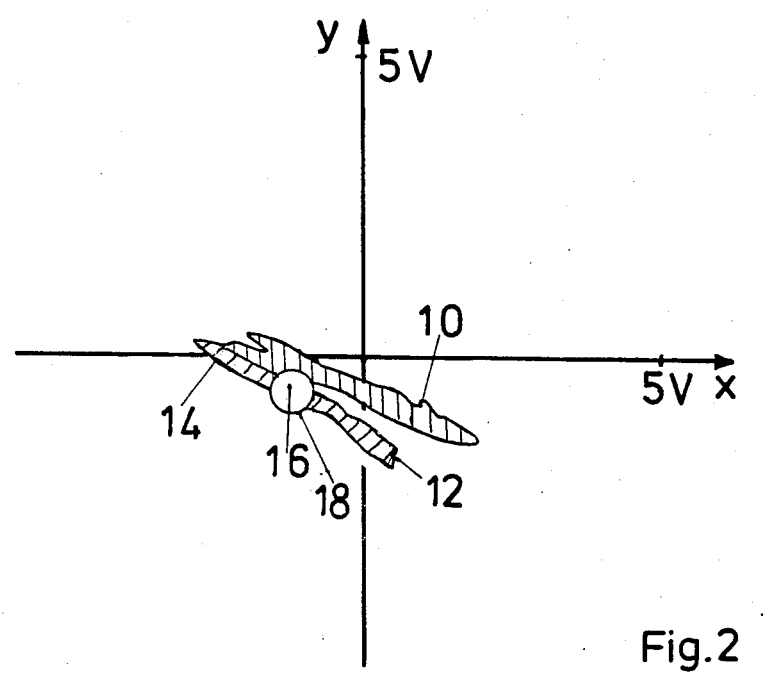
FIG. 2 is a graphical illustration of a Cartesian coordinate system showing a division of areas being assigned to the complex data of disturbance and flaw signals.

Certain complex values are not intended for further processing. These are such values corresponding to a range zero point 16, or which are close in value to zero point 16 as shown in FIG. 2. The limit for which complex data cannot be further processed is determined by a base threshold marked 18. Measured values within this base threshold 18 generally cannot supply information that can be sensibly processed. If a disturbance signal appears during the measuring cycle, then the first complex value starting from the base threshold 18 is within the range 10 assigned to the disturbance signals, which range is also traversed by the further complex data. The number of complex values falling within the range 10 is subject to the time rate at which the values are sampled from the output signal of the coil, to the relative motion between test object and the coil, and to the moment of formation of the disturbance signals within the given scanning cycle (i.e., acquisition time). Accordingly, complex data can run through curves within the range 14 before the range 12 is reached after passing through the zero range. If the order of sequence of passing through the ranges changes, then this indicates that there is no special type of disturbance signal present. While the complex values attributable to a pure disturbance signal pass through all of the ranges 10, 14 and 12, complex values will pass through only ranges 12 and 14 (and not range 10) if there is a flaw signal without a disturbance signal. In case disturbance signals and flaw signals are present at the same time, these range limits are bypassed in the preferred embodiment and thus it is automatically assumed that a flaw signal is present.

After having examined the position and the order of sequence of complex data received during a scanning operation as to the ranges 10, 12 and 14, one can determine for sure whether the measured values are attributable to only a disturbance signal, to a disturbance signal in connection with a flaw signal, or to only a flaw signal. Depending on these three possibilities, the complex values received in a scanning operation are stored and further selectively processed in different manners. If there is only a disturbance signal, the complex values can be erased or registered as such (since no flaws are present).

If a disturbance signal in connection with a flaw signal has been detected, then the disturbance signal component is suppressed. By means of the curve of the complex values, one can likewise detect the kind of the disturbance signal. Therefore, it is possible to provide suppressing arrangements adapted to the disturbing effects. The existing complex values are converted in a manner typical for the kind of disturbance so that the new values now contain only the signal components attributable to the flaw. However, a reduction of measuring accuracy may result when a disturbance signal and a flaw signal must be separated.

The flaw signals initially obtained without disturbance signals as well as the flaw signals from which disturbance signals have been removed are subsequently further processed. In a first step, the kind of flaw is detected by means of the typical curve of the complex data within the ranges 12 and 14. Preferably, the complex values are classified as to the following defects: hole, internal crack, external crack, and indefinable defects. Indefinable defects are not processed any further but rather are reported to the operators (by indicating the number of the test piece) for further testing using other techniques.

This defect classification is followed by a further step wherein the complex values obtained during a testing cycle are further processed. This step comprises the determination of the depth of the flaw. The depth dimension of flaws is evaluated by means of the detected type of flaw and the indication quantity (i.e., measured signal amplitude). The connection between indication quantity and depth dimension of flaws can be prorated and used for identification of the respective flaw depth from a given indication quantity.

The above described steps each utilize the complex values obtained from a scanning operation; they do not change them, however, insofar as they are again needed for a subsequent step of the method. In this subsequent method step one can refer, as far as necessary, to the originally generated complex data.

Figure 3:
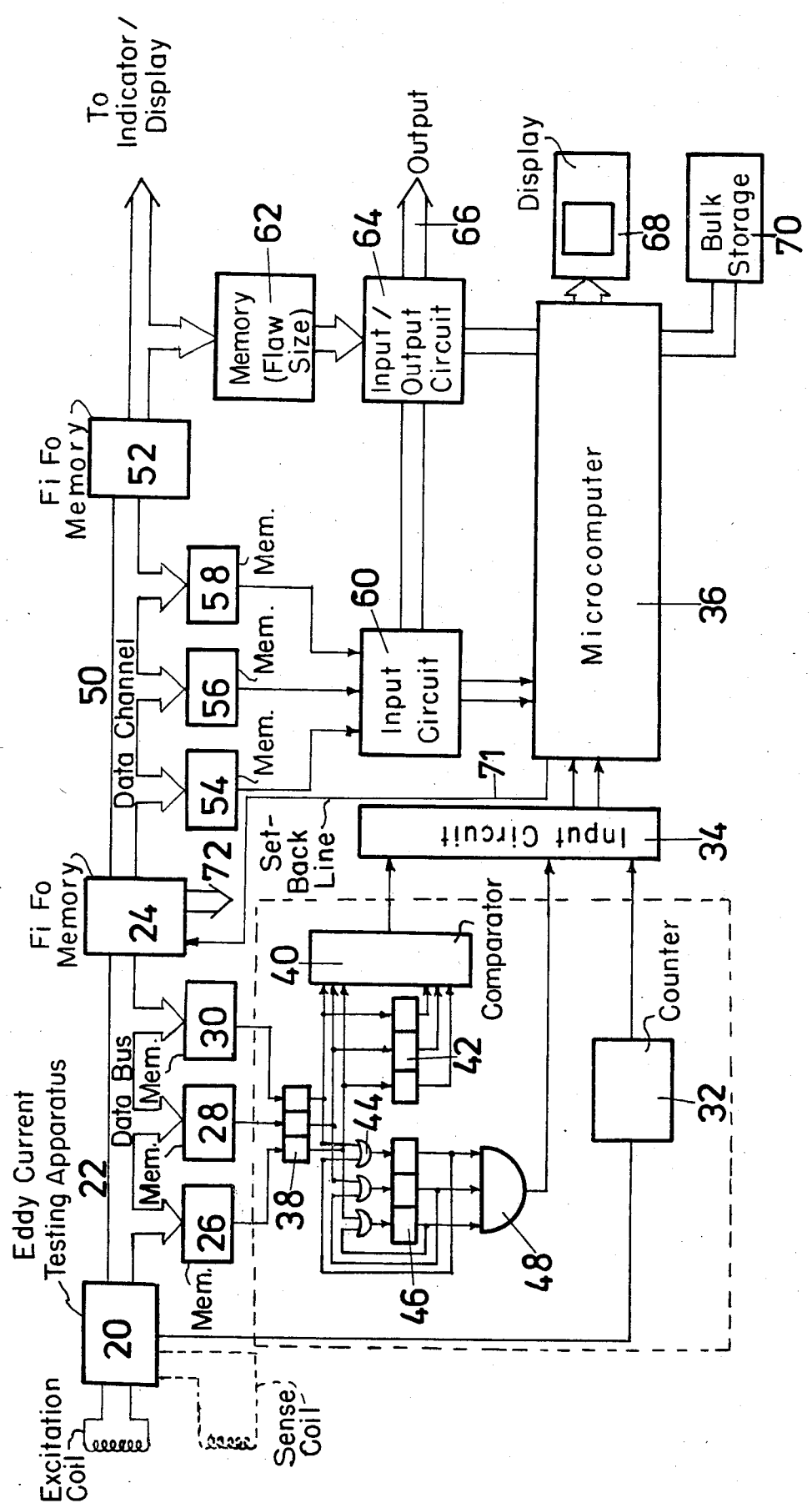
FIG. 3 is a block schematic diagram of an apparatus for testing materials with the eddy current principle in accordance with the present invention.

The apparatus shown in FIG. 3 for performing the above described steps includes a conventional eddy current testing apparatus 20 by means of which a test piece (not shown), e.g. a tube, is examined. During a test cycle the testing apparatus 20 feeds digital complex data to a data bus 22, which data corresponds to the output signal of the sensor coil of the testing apparatus 20.

The complex values so obtained (in a conventional manner) are fed to a RAM memory (stack) 24 operating according to the FIFO principle (first-in, first-out).

The complex values transmitted by the data bus 22 at the same time form addresses for three additional memories 26, 28, 30 preferably being designed as ROM memories. Each of the three memories 26, 28, 30 are assigned to a different one of the predetermined ranges 10, 12 and 14. A bit is stored in the memories 26, 28, 30 for each respective address indicating whether the complex measured value constituting the address falls within the respective range to which the memory is dedicated. In this manner, it is possible to assign the complex data very rapidly to the ranges. The base threshold 18 indicates a measure of how many digits must be available for the respective range per address in the memory 24.

With a data format corresponding to a twelve bit wide data bus 22, the most significant eight bits of data will suffice to exactly differentiate the range values from one another (many times, the most significant six bits of data will suffice).

The testing apparatus 20 is further connected to the counting input of a counter 32, which monitors the number of the complex values produced per scanning cycle. The counter 32 is preset to a value corresponding to the kind of possible disturbance signals, the scanning rate and the testing speed. The total number of complex values can also be regarded as a kind of code word in which the length is defined by the present value of the counter 32. The contents of counter 32, e.g., may be decremented by one with each new complex measured value. When the contents of the counter 32 reaches zero, the counter 32 applies a signal to an input circuit 34 of a microcomputer 36.

The outputs of the memories 26, 28, 30 each are connected to a respective storage cell of a first register 38. The outputs of the cells of the register 38 are connected to inputs of a comparator 40 and to inputs of storage cells of a second register 42. The outputs of register 42 are connected to the second inputs of the comparator 40. The comparator 40 compares the binary values at its inputs for the relationships of equality, greater than or less than.

The first register 38, via OR-interconnecting members 44, is connected to a third register 46, of which the outputs are likewise connected to inputs of the OR-interconnecting members 44. Further, the outputs of the steps of the third register 46 are in connection with the input circuit 34 via an AND-member 48. Whenever it is determined that only a disturbance signal is present, the data stored in the memory 24 is erased via the clear line 71 or can be registered via a bus 72 if desired.

When it is determined that signals other than a disturbance signal only are present, however, the outputs of the memory 24, via another data channel 50, are connected to inputs of a second FIFO-memory 52 and to inputs of three further memories 54, 56, 58, which can likewise be read only memories. The output signals of the memory 24, which are the complex values, serve likewise as addresses for the memories 54, 56, 58, which correlate between the complex values and those types of defects typical for them. For example, the contents of the cells of the memory 54 indicate the values belonging to specified addresses for holes in the test piece. The memories 56 and 58 contain the typical characteristics for internal cracks and external cracks. The outputs of the memories 54, 56, 58 each are connected to an additional input circuit 60 of the microcomputer 36.

The outputs of the memory 52 are applied to a further memory 62 being provided for the determination of the flaw size. At one's option, the memory 52 can also be connected to an indicating device (not shown). The outputs of the memory 62 are connected to the microcomputer 36 via an input/output circuit 64. The input/output circuit 64 has outputs 66 for controlling marking and/or sorting devices (or for use in other control functions) for the test pieces. The microcomputer 36 can further be connected to a viewing screen terminal 68 and to a large volume memory 70.

The registers 38, 42 and 46 e.g., are each composed of three storage cells (the number of storage cells is dependent on the number of ranges required for describing the signals, the ranges each being associated with one of the three memories 26, 28, 30 that are available for the three ranges 10, 12 and 14). When, during a measuring cycle, a complex measured value appears at the output of the testing apparatus, this value addresses the memories 26, 28 and 30. That memory corresponding to the range in which the complex measured value falls emits a signal to the series-connected memory cell of the register 38. In the preferred embodiment, the register 38 contains one signal for each output of testing apparatus 20, if the three ranges do not overlap (as is shown in FIGS. 1 and 2).

Register 42 stores e.g. the result of the testing of the preceding complex measured value. The comparator 40 determines whether the contents of the registers 38 and 42 are equal or whether the contents of the register 38 is larger or smaller than the contents of the register 42. Suppose that the digit with the lowest place value is assigned to the output of the memory 26. In this case, the output signal of the comparator indicates that the contents of the register 42 is smaller than that of the register 38, thus indicating a flaw signal is present.

If a test signal does not fall within any of the ranges defined by the memories 26, 28 and 30, then the value zero appears in the register 38. Via the comparator 40, this leads to the determination that there is a flaw signal.

Via OR-gate 44, the contents of the registers 38 and 46 are connected with one another in OR-operation. The result is again stored in the register 46. By means of this OR-operation, at the end of the measuring cycle in the register 46 all places are occupied by the same binary values when all ranges 10, 12, 14 have been traversed by the complex data. This is a criterion for determining that a disturbance signal together with a flaw signal is present in the path of the complex data. On the basis of this determination, the microcomputer 36 will release the contents of the memory 24 for further processing, consisting in the suppression of disturbance signals with subsequent classification of flaws via the memories 54, 56, 58. After the classification of flaws, the depth of the flaw is determined by means of the complex values via the memory 62.

If the number of ranges is more than three, more memories and register steps must be provided accordingly. The size (depth) of the FIFO-memories 24 and 52 must be adapted to the number of complex values produced by each measuring cycle. As to the data width of the measured values in the memory 52, the statements made above in connection with the memory 24 are applicable as well. The number of the memories connected to the input circuit 60 corresponds to the number of flaw types desired to be classified.

The counter 32 indicates the end of the measuring cycle to the computer 36. Then the microcomputer 36, while processing the output signals of the comparator 40, causes the utilization of the measured values present in the memory 24 for the classification of flaws and the simultaneous storing of same in the memory 52. If a disturbance signal is present, the information in the FIFO-memory 24 is erased via the set-back line 71 or, in case storage of all disturbance data is desired, is made available for registration via a separate data bus 72. Thereafter, the microcomputer 36 will direct the evaluation of the depth of flaws by means of the flaws classified each time.

The arrangement shown in FIG. 3 enables the processing of an individual complex measured value in approximately 10 microseconds. Thus, the processing time is essentially shorter than the measuring gate times of the individual measuring frequencies. With a testing apparatus 20 generating several frequencies in the 1 kHz range, fifteen measured values require approximately 15 msecs for generation. If the processing of these measured values takes place at the given system clock pulse, then this time will appear with each of the above described method steps. Consequently the result of the processing will be available with a delay of approximately 50 msecs. This time is so short that even in case a flaw is detected at the end of the test piece, there is still sufficient time for selection by a marking or sorting device.

We claim:

1. A method for detecting flaws in electrically conductive material comrpising the steps of:
    (1) inducing magnetic fields in a material to be tested for flaws, thereby causing eddy currents to flow in said material;
    (2) detecting the magnetic fields in proximity to said material and producing electrical signals in response thereto;
    (3) converting said electrical signals produced by said detecting step (2) to at least one initial digital value representing a complex number;
    (4) characterizing said initial value produced by said converting step (3) as being included in one of three ranges, a value included in a first of said three ranges corresponding to a field produced by phenomena other than a flaw in said material, a value included in a second of said three ranges corresponding to a field produced in part by a flaw in said material and in part by phenomena other than said flaw in said material, a value included in a third of said three ranges corresponding to a field produced only by a flaw in said material;
    (5) removing components from said initial value attributable to phenomena other than a flaw in said material to produce a processed value if said characterizing step (4) characterizes said initial value as being included in said second range;
    (6) if said characterizing step (4) characterizes initial values being included in said third range, determining parameters of a flaw in said material in response to said initial value; and
    (7) if said characterizing step (4) characterizes said initial value as being included in said second range, determining parameters of a flaw in said material in response to said processed value produced by said removing step (5).

2. A method as in claim 1 wherein said determining steps (6) and (7) each include the steps of:
    (a) determining the configuration of said flaw; and
    (b) determining the size of said flaw.

3. A method as in claim 1 wherein:
    said method further includes the steps of:
        (a) repeating said steps (1)–(3) for magnetic fields having different characteristics to produce a sequence of initial values, and
        (b) performing said step (4) for each of said values in said sequence; and
    said determining steps (6) and (7) together comprise the step of determining the parameters of a flaw in said material in response to a plurality of said processed values and/or a plurality of initial values included in said third range and in response to the order to said values in said sequence.

4. A method as in claim 3 wherein:
    said repeating step (a) includes the step of storing said sequence of values; and
    said performing step (b) is performed subsequent to said repeating step (a) and includes the step of chracterizing said values stored by said storing step in order of the sequence in which said values are produced by said converting step (3).

5. A method as in claim 3 wherein said characterizing step (4) includes the steps of:

(a) defining a first range (10) of values corresponding to fields produced by phenomena other than a flaw in said material;
(b) defining a second range (12) of values corresponding to fields produced by a flaw in said material;
(c) defining a third range (14) of values corresponding to the intersection of first and second ranges;
(d) determining, for each of said values in said sequence, which of said first, second and third ranges includes said values;
(e) determining said fields detected by said detecting step (2) are generated only by eddy currents flowing due to flaws in said material if none of said values in said sequence are included in said first range; and
(f) determining said fields detected by said detecting step (2) are generated by both eddy currents flowing due to flaws in said material and by phenomena other than flaws in said material if different ones of said values in said sequence are included in said first, second and third ranges.

6. A method as in claim 5 further including the steps of:
defining a base threshold range (18) of predetermined size intersecting at least one of said first, second and third ranges; and
inhibiting said characterizing step (4) for values included in said base threshold range.

7. A method as in claim 5 wherein said determining steps (6) and (7) each include the step of determining said parameters of a flaw in response to the order in said sequence of adjacent values included in different ones of said first, second and third ranges.

8. An apparatus for detecting flaws in electrically conductive material comprising:
means for inducing magnetic fields in a material to be tested for flaws, thereby causing eddy currents to flow in said material;
means for detecting the magnetic fields, induced by said inducing means, in proximity to said material and producing eletrical signals in response thereto;
means for converting said electrical signals, received from said detecting means, to at least one initial digital value representing a complex number;
means for characterizing said initial value, received from said converting means, as included in one or more of three ranges, a value included in a first of said three ranges corresponding to a field produced by phenomena other than a flaw in said material, a value included in a second of said three ranges corresponding to a field produced in part by a flaw in said material and in part by phenomena other than a flaw in said material, a value included in a third of said three ranges corresponding to a field produced only by a flaw in said material;
means for removing components attributable to phenomena other than a flaw in said material from said initial value, received from said characterizing means, to produce a processed value if said characterizing means characterizes said initial value as included in said second range; and
means for determining parameters of a flaw in said material in response to said initial value if said characterizing means characterizes said initial value as being included in said third range and in response to said processed value produced by said removing means if said characterizing means characterizes said initial value as being included in said second range.

9. An apparatus as in claim 8 wherein said determining means includes:
means for determining the configuration of said flaw; and
means for determining the size of said flaw.

10. An apparatus as in claim 8 wherein:
said apparatus further includes control means for controlling said inducing means to induce in said material a sequence of magnetic fields having different characteristics, thereby causing said converting means to sequentially produce a plurality of different initial digital values, and for controlling said characterizing means to characterize each of said values in said sequence; and
said determining means includes means for determining the parameters of a flaw in said material in response to a plurality of said processed values and/or a plurality of initial values included in said third range and in response to the order of said values in said sequence.

11. An apparatus as in claim 10 wherein:
said apparatus further includes means for storing said sequence of values in the order of the sequence in which said values are produced by said converting means; and
said characterizing means is responsive to said sequence of values stored by said storing means.

12. An apparatus as in claim 10 wherein said characterizing means includes:
means for defining a first range (10) of values corresponding to fields produced by phenomena other than a flaw in said material;
means for defining a second range (12) of values corresponding to fields produced by a flaw in said material;
means for defining a third range (14) of values corresponding to the intersection of the first and second ranges;
means, operatively coupled to said first range defining means, second range defining means and third range defining means, for determining, for each of said values in said sequence, which of said first, second and third ranges includes said values; and
determining means for characterizing said fields detected by said detecting means as being generated only by eddy currents flowing due to flaws in said material whenever none of said values in said sequence are included in said first range, and for characterizing said fields detected by said detecting means as being generated by eddy currents flowing due to a flaw in said material and by phenomena other than flaws in said material if different ones of the values in said sequence are included in said first, second and third ranges.

13. An apparatus as in claim 12 further including:
means for defining a base threshold range (18) of predetermined size intersecting at least one of said first, second and third ranges; and
means for producing an inhibiting signal whenever one of said values in said sequence is included in said base threshold range,
wherein said characterizing means is inhibited in response to said inhibiting signal.

14. An apparatus as in claim 12 wherein said determining means includes means for determining said parameters of a flaw in response to the order in said sequence of adjacent values included in different ones of said first, second and third ranges.

* * * * *